US00PP15866P2

(12) United States Plant Patent
Kawashima

(10) Patent No.: US PP15,866 P2
(45) Date of Patent: Jul. 19, 2005

(54) ***OSTEOSPERMUM* PLANT NAMED 'KAKEGAWA AU11'**

(50) Latin Name: *Osteospermum fruticosum*
Varietal Denomination: Kakegawa AU11

(75) Inventor: Moriya Kawashima, Matsumoto (JP)

(73) Assignee: Sakata Seed Corporation, Yokohama (JP)

( * ) Notice: Subject to any disclaimer, the term of this patent is extended or adjusted under 35 U.S.C. 154(b) by 141 days.

(21) Appl. No.: 10/775,618

(22) Filed: Feb. 10, 2004

(51) Int. Cl.[7] ..... A01H 5/00
(52) U.S. Cl. ..... Plt./360
(58) Field of Search ..... Plt./360

*Primary Examiner*—Anne Marie Grunberg
*Assistant Examiner*—June Hwu
(74) *Attorney, Agent, or Firm*—Jondle & Associates P.C.

(57) ABSTRACT

An *Osteospermum* cultivar particularly distinguished by its light pink flower color and tendency to hold flowers open later in the evening.

1 Drawing Sheet

Genus and species: *Osteospermum fruticosum.*
Variety denomination: 'Kakegawa AU11'.

BACKGROUND OF THE NEW PLANT

The variety 'Kakaegawa AU11' originated from a gene pool population made in 1999 in Misato, Japan. In May 1999, three varieties were intercrossed and seed from these three plants were bulked to make the population. The three varieties were 'Kakegawa AU4' (U.S. Plant Pat. No. 12,812), 'Purple Passion' (unprotected, now only available in 'Passion Mix') and an unnamed breeding line of unknown origin. The unnamed breeding line possessed yellow flowers, an erect plant habit and very vigorous rooting. It is not known which two varieties were the actual parents for 'Kakegawa AU11'. Seed from this population was sown in April 2000 and plants were transplanted to the outdoor field. In August 2000, single-plant selections were made for vegetative propagation using flower color, compact plant habit and strong rooting as selection criteria. One selection, designated breeder code M2-72, became the new variety 'Kakegawa AU11'. The variety 'Kakegawa AU11' was found to be stable and reproduce true to type in successive generations of asexual propagation.

DESCRIPTION OF PHOTOGRAPHS

This new *Osteospermum* plant is illustrated by the accompanying photographs which show blooms and foliage of the plant in full color. The colors shown are as true as can be reasonably obtained by conventional photographic procedures.

DESCRIPTION OF THE NEW CULTIVAR

Figure 1:
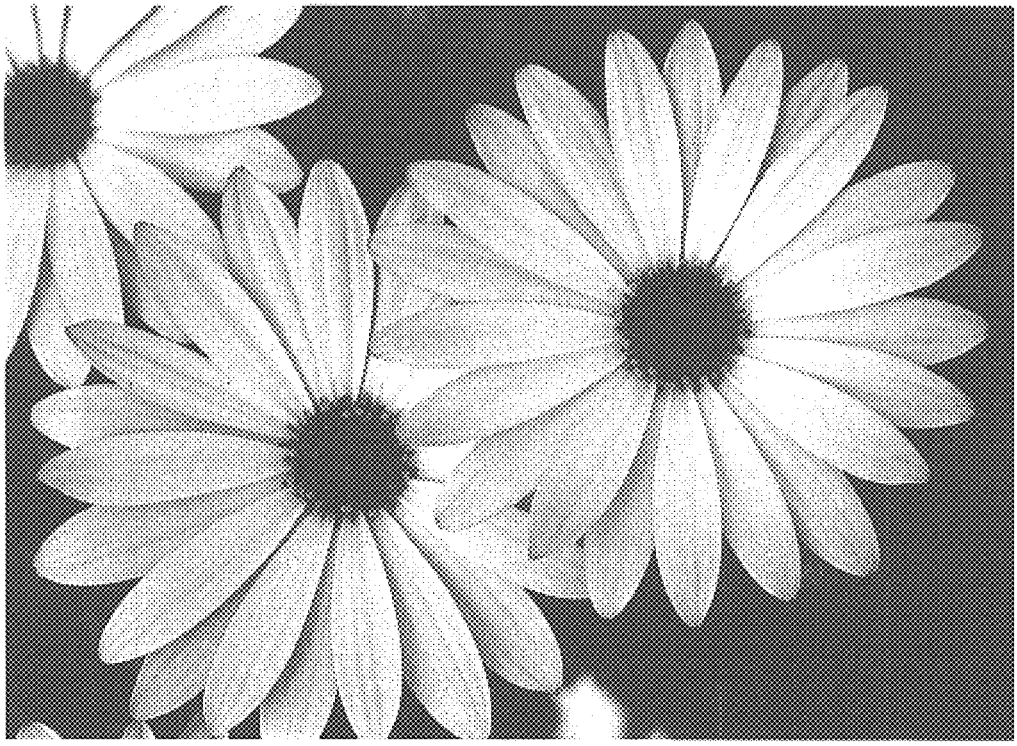
FIG. 1 shows a close-up view of several inflorescences.
Figure 2:
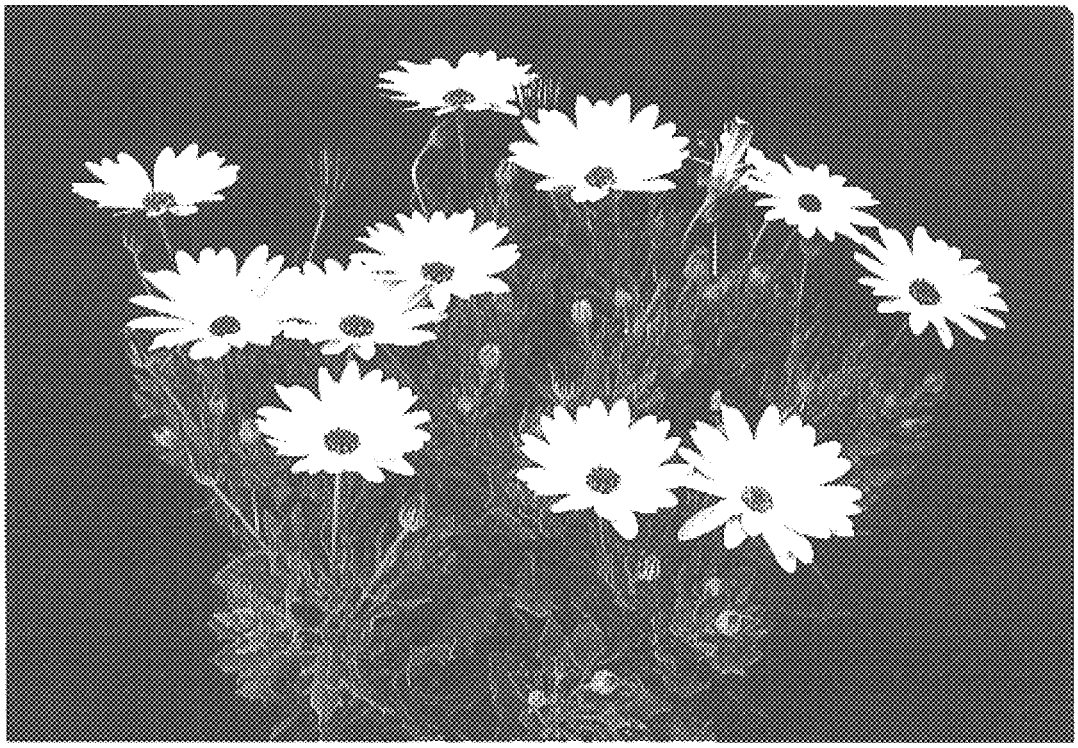
FIG. 2 shows a side view of the entire plant including its flower buds, opened blooms and foliage.

The following detailed descriptions set forth the distinctive characteristics of 'Kakegawa AU11'. The data which defines these characteristics were collected from asexual reproductions carried out in Salinas, Calif. Data was collected on plants 28 weeks from transplanting rooted cuttings into 16 cm diameter pots, one plant per pot. Color references are to The R.H.S. Colour Chart of The Royal Horticultural Society of London (R.H.S.).

DESCRIPTION OF THE NEW PLANT

Classification:
*Family.*—Compositae.
*Botanical.*—*Osteospermum fruticosum.*

Parentage: The female and male parents are unknown. This variety was selected from a gene pool population that was created by intercrossing the varieties 'Kakegawa AU4' (U.S. Plant Pat. No. 12,812), 'Purple Passion' (unprotected, now only available in 'Passion Mix') and an unnamed breeding line with purple flowers, an erect plant habit and very vigorous growth.

Growth:

*Time to produce a rooted cutting.*—Cuttings will colonize a 2.5 cm diameter by 2.5 cm tall greenhouse tray cell with peat-based plant media in approximately five weeks. Cuttings are dipped in a normal dilution (1.9) of DIP 'N GROW root inducing solution in water. The trays are misted hourly during rooting.

*Environmental conditions for plant growth.*—Rooted cuttings are transplanted to pots with a 16 cm diameter, one plant per pot. Peat moss-based growing media is used. The pots are watered using a 150–200 ppm fertilizer solution containing 18% nitrogen, 8% phosphorus and 18% potassium. The soil is allowed to dry between waterings. During the first few weeks after transplanting the plants should have evening temperatures around 15–18° C. for good root growth. When plants reach 7.5–10 cm in height they are pinched back to 5–6 leaves to promote branching. The plants are grown through the winter in cool greenhouses (10–15° C.) with no shading to keep their habit compact. In spring, after the plants have received at least four weeks of cool conditions to vernalize, warmer temperatures can be used to promote blooming. Spring and summer daytime high temperatures in Salinas, Calif., where the data was collected, range from 16–25° C.

*Time to bloom from propagation.*—18–20 weeks when rooted vegetative cuttings are transferred to a six-inch diameter pot in late fall and given several weeks of below 50 degree Fahrenheit temperature prior to increasingly warmer spring weather. Flowering season is in April through June and is temperature (required to initiate bud development) and day length dependent (long days). They will stop flowering when temperatures are too high, such as in the southern areas of the country.

*Habit.*—Upright and branching.

*Life cycle.*—Perennial.

Plant:

*Form.*—Branching, dense.

*Plant size.*—Height is 64–90 cm; width 46–64 cm.

Stems:

*Anthocyanin color.*—Greyed-purple (RHS 187A).

*Internode length.*—0.8–1.0 cm.

*Stem color.*—Yellow-green (RHS 145A).

*Stem description.*—Strong, erect.

*Stem diameter.*—5.0–6.0 mm.

*Pubescence.*—Glabrous.

*Pubescence shape.*—Linear.

*Pubescence color.*—White (RHS N155A).

Leaves:

*Arrangement.*—Alternate.

*Shape.*—Oblanceolate.

*Apex.*—Acute.

*Base.*—Decurrent.

*Margin.*—Serrate.

*Venation.*—Pinnate.

*Surface.*—Dull, rough.

*Surface pubescence.*—Slight, white (RHS N155A).

*Length.*—5.5–8.5 cm.

*Width.*—2.0–3.5 cm.

*Thickness.*—1.0 mm.

*Color.*—Upper is green (RHS 139A); Lower is yellow-green (RHS 146A).

*Venation color.*—Upper is yellow-green (RHS 144A); Lower is yellow-green (RHS 146B).

Inflorescence:

*Type.*—Capitulum (head); disc florets are staminate and ray florets are carpellate.

*Diameter.*—7.0–8.0 cm.

*Depth.*—2.5–3.0 cm.

*Petal numbers.*—18–22.

*Disc diameter.*—1.3 cm.

*Disc floret number.*—65–70.

*Flowering habit.*—Determinate.

*Flowers life span.*—3–4 days.

*Fragrance.*—None.

*Seed production.*—None.

*Peduncle length.*—6.0–7.0 cm.

*Peduncle diameter.*—2.0 mm.

*Peduncle color.*—Yellow-green (RHS 144A).

*Peduncle texture.*—Rough, pubescent.

*Phyllaries.*—18–22 per inflorescence, free, arranged symmetrically; Length — 1.2–1.5 cm; Width — 2.0 mm; Apex — Acute; Margin — Entire; Shape — Linear, acute tip; Color — Upper, yellow-green (RHS 146B); Lower, yellow-green (RHS 146C).

Ray florets:

*Corolla.*—One petal per ray floret. Only the outer row of florets are the ray florets.

*Petals length.*—3.8–4.0 cm.

*Petal width.*—0.8–1.0 cm.

*Petal shape.*—Spatulate.

*Petal apex.*—Acute.

*Petal margin.*—Entire.

*Petal color.*—Upper, purple (RHS 75B) fading to white (RHS N155A) near the base; Lower, yellow (RHS 10D), center stripe 2.0 mm purple (RHS 77C).

*Petal pubescence.*—None.

*Pistil number.*—1, compound.

*Pistil length.*—0.5 mm.

*Stigma form.*—One style with two stigma branches.

*Stigma color.*—Purple (RHS N77C).

*Style color.*—White (RHS N155A).

Disc florets:

*Color.*—(Color at top, as seen looking at inflorescence) yellow-green (RHS 144A).

*Shape.*—Tubular.

*Apex.*—Acute.

*Surface.*—Pubescent, dull.

*Size.*—Length 1.2–1.4 cm; width 0.8–1.0 mm.

*Stamens.*—5, fused into a single tube.

*Anther color.*—Purple (RHS 79A).

*Pollen color.*—Yellow-orange (RHS 23B).

DISEASE AND INSECT RESISTANCE

'Kakegawa AU11' is very disease resistant but it can be susceptible to aphids, thrips, whiteflies and worms.

COMPARISON WITH KNOWN CULTIVARS

'Kakegawa AU11' is a distinct variety of *Osteospermum* owing to the creamy, off-white color the flower have when they first open. As the flowers mature, they turn to a light pink color at the upper portion of the petals and strongly fade into a light white at the base portion. This new variety differs from the varieties 'Kakegawa AU4' and 'Purple Passion' mainly in flower color. 'Kakegawa AU4' has yellow flowers and 'Purple Passion' has purple flowers. 'Kakegawa AU11' is most similar to the variety 'Kakegawa AU2', the subject of U.S. Plant Pat. No. 12,795; however, there are numerous differences as shown in Table 1 below.

TABLE 1

| Trait | 'Kakegawa AU11' | 'Kakegawa AU2' |
|---|---|---|
| Petals | Light pink petal with shades of purple (RHS 75B) on the upper portion and white (RHS N155B) at the petal base | Purple (RHS N78C) petals with white (RHS N155A) at the base |
| Leaf Apex | Acute with faint signs of pointed tip | Rounded with no visible signs of tapering |
| Pollen Color | Yellow-green (RHS 23B) | Yellow-orange (RHS 21A) |
| Inflorescence Diameter | 7.0–8.5 cm | 5.0–6.0 cm |

I claim:

1. A new and distinct cultivar of *Osteospermum* plant as shown and described herein.

* * * * *